United States Patent [19]
Bell et al.

[11] Patent Number: 5,411,541
[45] Date of Patent: May 2, 1995

[54] PORTABLE FLUID THERAPY DEVICE

[75] Inventors: Anthony H. G. Bell, Laguna Niguel; Carl E. Prindle, South Laguna Beach, both of Calif.

[73] Assignee: Oansh Designs Ltd., Zurich, Switzerland

[21] Appl. No.: 103,293

[22] Filed: Aug. 5, 1993

[51] Int. Cl.⁶ .............................. A61F 7/00
[52] U.S. Cl. ...................... 607/104; 607/108; 601/15
[58] Field of Search .............. 607/96, 104, 108, 109, 607/111, 114; 128/24 R; 602/2, 14; 601/15, 148–152

[56] References Cited

U.S. PATENT DOCUMENTS

| | | | |
|---|---|---|---|
| 222,690 | 12/1879 | Goldschmidt | 607/104 |
| 1,914,026 | 6/1933 | Kirk | 607/104 |
| 3,548,819 | 12/1970 | Davis . | |
| 3,561,435 | 2/1971 | Nicholson . | |
| 3,628,537 | 12/1971 | Berndt . | |
| 3,683,902 | 8/1972 | Artmenko et al. . | |
| 3,717,145 | 2/1973 | Bendt et al. . | |
| 3,867,939 | 2/1975 | Moore et al. | 607/104 |
| 3,871,381 | 3/1975 | Roslonski . | |
| 4,121,582 | 10/1978 | Remiro | 607/108 |
| 4,253,449 | 3/1981 | Arkans et al. | 128/24 R |
| 4,259,961 | 4/1981 | Hood, III . | |
| 4,338,944 | 7/1982 | Arkans . | |
| 4,523,594 | 6/1985 | Kuznetz . | |
| 4,621,624 | 11/1986 | Rayboy . | |
| 4,677,970 | 7/1987 | Green et al. . | |
| 4,821,354 | 4/1989 | Little | 607/104 |
| 4,928,678 | 5/1990 | Grim . | |
| 4,953,550 | 9/1990 | Dunshee | 607/114 |
| 4,962,761 | 10/1990 | Golden . | |
| 5,062,414 | 11/1991 | Grim | 607/108 |
| 5,072,875 | 12/1991 | Zacoi . | |
| 5,074,285 | 12/1991 | Wright . | |
| 5,080,089 | 1/1992 | Mason . | |
| 5,097,829 | 3/1992 | Quisenberry | 607/104 |
| 5,172,689 | 12/1992 | Wright . | |
| 5,174,285 | 12/1992 | Fontenot | 607/104 |
| 5,190,032 | 3/1993 | Zacoi . | |
| 5,230,335 | 7/1993 | Johnson, Jr. et al. . | |
| 5,241,951 | 9/1993 | Mason et al. | 607/104 |

FOREIGN PATENT DOCUMENTS 2115392 12/1973 Germany ............ 607/108

OTHER PUBLICATIONS

"Instructional Course Lectures", American Academy of Orthopedice Surgeons, vol. 42 1993.
"Dual-Temp, Localized Cold/Heat Therapy Unit" Product Manual for Seabrook Medical Systems, Inc.

Primary Examiner—Richard J. Apley
Assistant Examiner—Jeanne M. Mollo
Attorney, Agent, or Firm—Stetina Brunda & Buyan

[57] ABSTRACT

A portable fluid therapy device comprising a flexible bladder member defining independently inflatable inner and outer chambers. Fluidly coupled to inlet and outlet valve ports of the inner chamber is a portable water pumping apparatus for selectively infusing hot or cold water into the inner chamber or circulating the water therethrough, The bladder member is adapted to be used in association with a brace member or cast and may be configured to accommodate a desired region of the body.

10 Claims, 5 Drawing Sheets

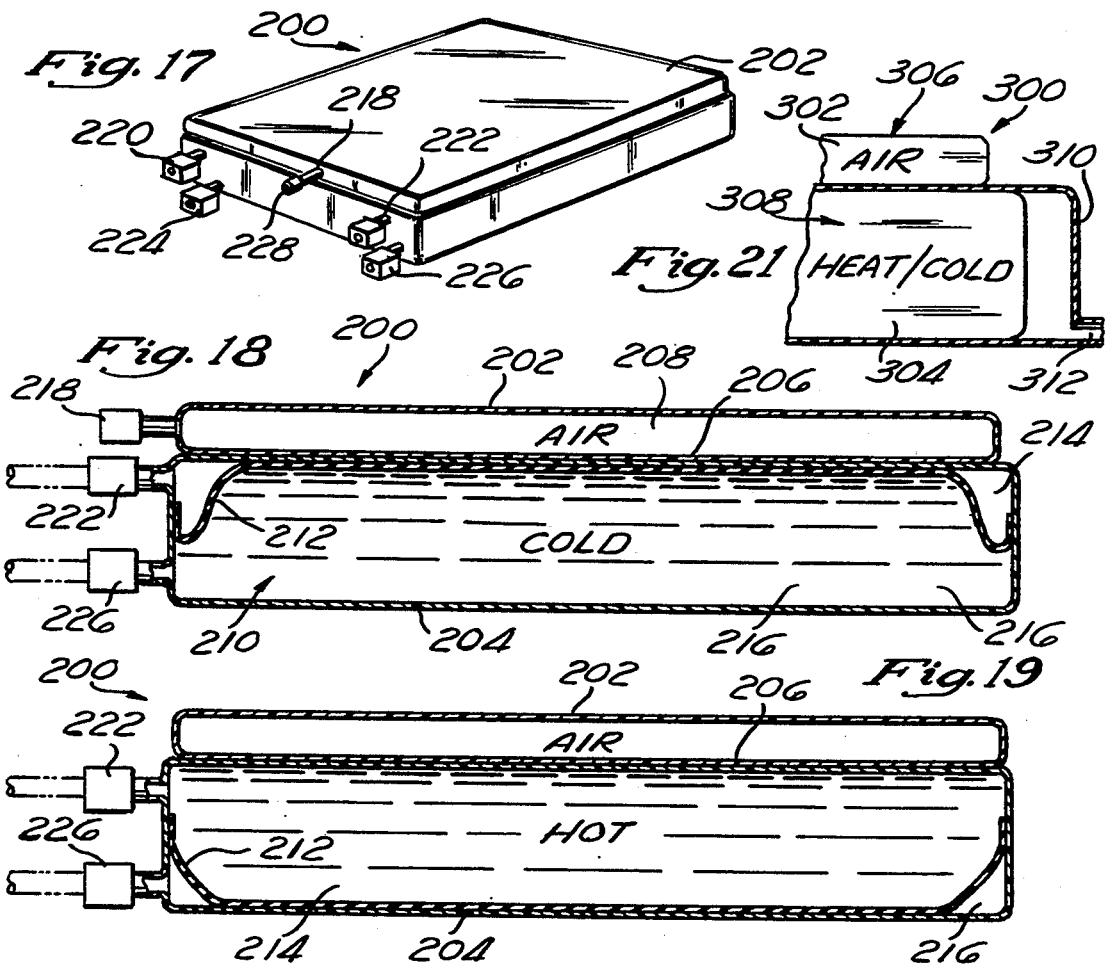
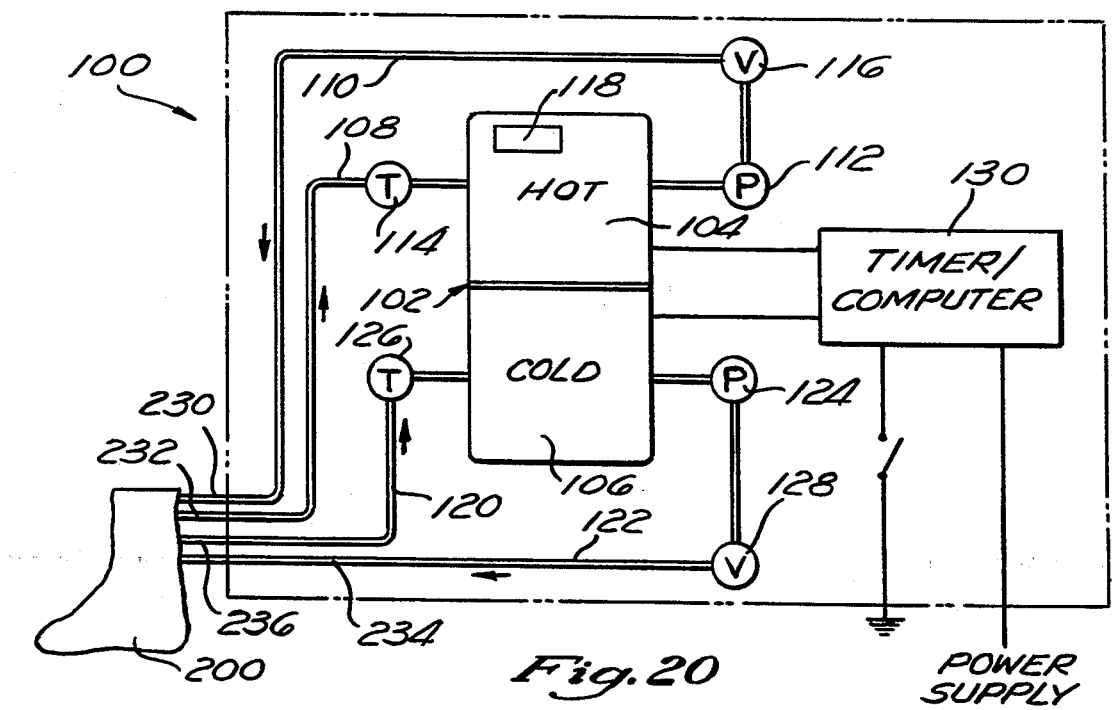

PORTABLE FLUID THERAPY DEVICE

FIELD OF THE INVENTION

The present application is related to application Ser. No. 07/933,328, now U.S. Pat. No. 5,317,820 entitled MULTI-APPLICATION ANKLE SUPPORT FOOTWEAR and filed on Aug. 21, 1992, the disclosure of which is expressly incorporated herein by reference. The present invention relates generally to therapeutic devices, and more particularly to a bladder member defining independently inflatable inner and outer chambers which is used for the application of hot or cold therapy to desired regions of the body.

BACKGROUND OF THE INVENTION

Therapeutic modalities are physical agents used to reduce pain and swelling and to help restore range of motion, strength, and function following an injury. Two of the fundamental modalities used to treat injury are heat and cold. Both cold and heat therapy have been found to be clinically effective in accelerating the healing of damaged tissue. Particularly, cold therapy acts to retard metabolism within the tissue cells, whereas heat therapy accelerates cellular metabolism. Often, physicians and therapists prescribe use of both modes of therapy alternately. In this regard, both heat and cold therapy are of particular value because of their effect on the pain and inflammation that occur as a response to injury.

Thermal therapy is the treatment of diseases by raising the temperature of the tissue. The mechanisms by which this is accomplished are threefold, i.e. conduction, convection, and radiation. Conduction is direct contact, such as occurs with the application of a hot pack. In convection, a medium such as hot air or water is applied around the injured part, as in a whirlpool. In radiation, a source of warmth, such as a heat lamp, is used to heat the body part. Heat produces analgesia by diminishing the afferent pain impulses, causes vascular dilation that improves the blood supply, and increases the metabolic rate by speeding up the rate of enzymatic reactions. Heat also increases collagen extensibility, which improves overall flexibility and enhances motion. Finally, heat causes a decrease in muscle tone and muscle spasm. As such, localized heat therapy is of particular benefit with orthopedic conditions such as lower back pain, strains, acute injuries, chronic pain, muscle spasm, tendinitis, and arthritis. Heat therapy is also prescribed for skin trauma (bruises, contusions, abscesses, boils, burns) and other medical problems like infection, phlebitis, I.V. infiltration, and neuritis.

Cryotherapy is the use of cold to treat injury or disease. The consensus among medical professionals is that cold is a standard treatment for both immediate care and for rehabilitation following most soft-tissue injuries. Cold works by its effects on metabolism, circulation, inflammation, and edema. Because cold slows enzymatic function and, hence, metabolic reactions, any metabolic reaction association with inflammation is inhibited and its effects are mitigated. Cold also causes vasoconstriction which, though not preventing hemorrhage, prevents the extension of hematoma.

The application of cold also increases collagen stiffness, thereby decreasing the extensibility of tendons and ligaments, and delays, but does not eliminate, inflammation. Edema is reduced, usually as a result of the use of cold together with compression and elevation. In addition to decreasing the temperature of skin, subcutaneous tissue, muscles and joints, the application of cold relieves pain by slowing or blocking nerve impulses, and also decreases muscle spasm. With the decrease in pain and muscle spasm, early mobilization and exercise can be undertaken more comfortably. Typically, cold is applied by the use of ice massage or ice baths, as well as through the use of gel refrigerator chemical packs (which produce an endothermic reaction) and refrigerant compression machines.

Advantageously, cold applications used during rehabilitation allow immediate mobilization and make it easier for the patient to begin therapeutic exercise. Localized cold therapy is often used in the operating room, the recovery room, the intensive care unit, in physical therapy and in individual patient rooms. It is used effectively to treat surgical incisions, as well as wound and inflammation caused by traumatic injury. With regard to surgical applications, cold therapy is often prescribed in relation to orthopedic, neurologic/orthopedic, abdominal, oral, ufological and obstetrical/gynecological surgery. In most cases, cold therapy is applied immediately following the surgical procedure, directly to the wound site. This acts to reduce swelling and pain, while also reducing or eliminating the need for pain-killing medications.

For the specialty of hand surgery, cold therapy is also applied to the upper extremity before and during the procedure in conjunction with a tourniquet. This is done to extend the surgical period beyond the normal time limit by decreasing the adverse effects of tourniquet ischemia. Other conditions indicating the application of cold therapy include acute injuries, bruises/contusions, chronic pain, muscle spasm, strains, arthritis, cellulitis, lower back pain, sprain and alopecia. Both cold and heat therapy are also used extensively outside the hospital in physician's offices and out-patient clinics.

Due to the numerous advantages attendant to the use of cold and heat therapy for therapeutic applications, various prior art medical devices have been developed to facilitate such application. However, many of these prior art devices lack portability and are adapted for use solely in environments such as a hospital, a physician's office, or an out-patient clinic. Additionally, many of these devices and systems are difficult to use and expensive, thus making their use impractical by an untrained individual in an environment such as the home. The present invention addresses these shortcomings by providing an inexpensive, portable fluid therapy device for the application of heat or cold therapy to a desired region of the body which may be utilized in the home to facilitate desired therapeutic treatment.

SUMMARY OF THE INVENTION

In accordance with a preferred embodiment of the present invention, there is provided a portable fluid therapy device comprising a flexible bladder member defining independently inflatable inner and outer chambers. In the preferred embodiment, the bladder member comprises inner and outer walls having an intermediate wall positioned therebetween. The outer chamber is defined between the outer and intermediate walls, with the inner chamber being defined between the inner and intermediate walls. Fluidly coupled to the inner chamber is an inlet valve port and an outlet valve port, while fluidly coupled to the outer chamber is an inlet/outlet valve port. Formed in the inner wall are a multiplicity of recessed portions which are used to channel fluid through the inner chamber from the inlet to the outlet valve ports thereof, and to prevent the inner wall from bulging excessively when the inner chamber is filled with fluid.

In the preferred embodiment, the outer chamber is adapted to be selectively inflated with air via a handheld air pump which is fluidly connectable to the inlet/outlet valve port thereof. The inlet/outlet valve port preferably includes a purge mechanism to prevent the over-inflation of the outer chamber. The inner chamber is adapted to be filled with hot or cold water via a portable water pumping apparatus which is fluidly connectable to the inlet valve port. The water pumping apparatus is also fluidly connectable to the outlet valve port for purposes of circulating water through the inner chamber.

The portable water pumping apparatus itself comprises a housing having at least one insulated water-retaining reservoir disposed therewithin. Fluidly coupled to the reservoir are inlet and outlet lines which have ends protruding from the housing. Disposed within the housing and fluidly coupled within the outlet line is a pump which is adapted to circulate water from the reservoir through the inner chamber of the bladder member via the inlet and outlet lines when activated. A temperature gauge is fluidly coupled to the inlet line for displaying temperature readings corresponding to the temperature of the water flowing from the inner chamber, through the inlet line, and back into the reservoir. In addition to the pump, also fluidly coupled to the outlet line is an adjustable flow control valve which is adapted to regulate the flow of water therethrough. The water pumping apparatus also includes a programmable control unit disposed within the housing which is electrically interfaced to the pump and temperature gauge, and is adapted to coordinate the functions and operations thereof. To facilitate the portability of the water pumping apparatus, attached to the housing is a handle member.

In the preferred embodiment, the bladder member is fabricated from a flexible material selected from the group consisting of rubber, vinyl, urethane and polyvinyl chloride. Additionally, the bladder member is typically used in combination with the brace member for maintaining the bladder member in a desired orientation relative to and in abutting contact with a selected region of the body.

Further in accordance with the present invention, there is provided a method for therapeutically treating a desired region of the body. The preferred method comprises the steps of positioning a bladder member defining independently inflatable inner and outer chambers against the body region in a manner wherein the inner chamber is disposed closest thereto. Thereafter, the outer chamber is inflated with air via an inlet/outlet valve port fluidly coupled thereto, with water being infused into the inner chamber via an inlet valve port fluidly coupled thereto. The preferred method further comprises the step of circulating water through the inner chamber via the coupling of a water pumping apparatus to the inlet valve port and an outlet valve port also fluidly coupled to the inner chamber. The water pumping apparatus may be cycled on and off to create a pulsing effect as the water is circulated through the inner chamber.

BRIEF DESCRIPTION OF THE DRAWINGS

These as well as other features of the present invention will become more apparent upon reference to the drawings wherein:

FIG. 10 is a perspective view of a calf embodiment of the bladder member;

FIG. 18 is a cross-sectional view of the bladder member shown in FIG. 17;

FIG. 19 is a cross-sectional view of the bladder member shown in FIG. 17;

FIG. 20 is a schematic illustrating the operation of a fluid therapy device incorporating a water pumping apparatus constructed in accordance with a second embodiment of the present invention; and FIG. 21 is a partial cross-sectional view of a flexible bladder member constructed in accordance with a third embodiment of the present invention.

DETAILED DESCRIPTION OF THE PREFERRED EMBODIMENTS

Figure 1:
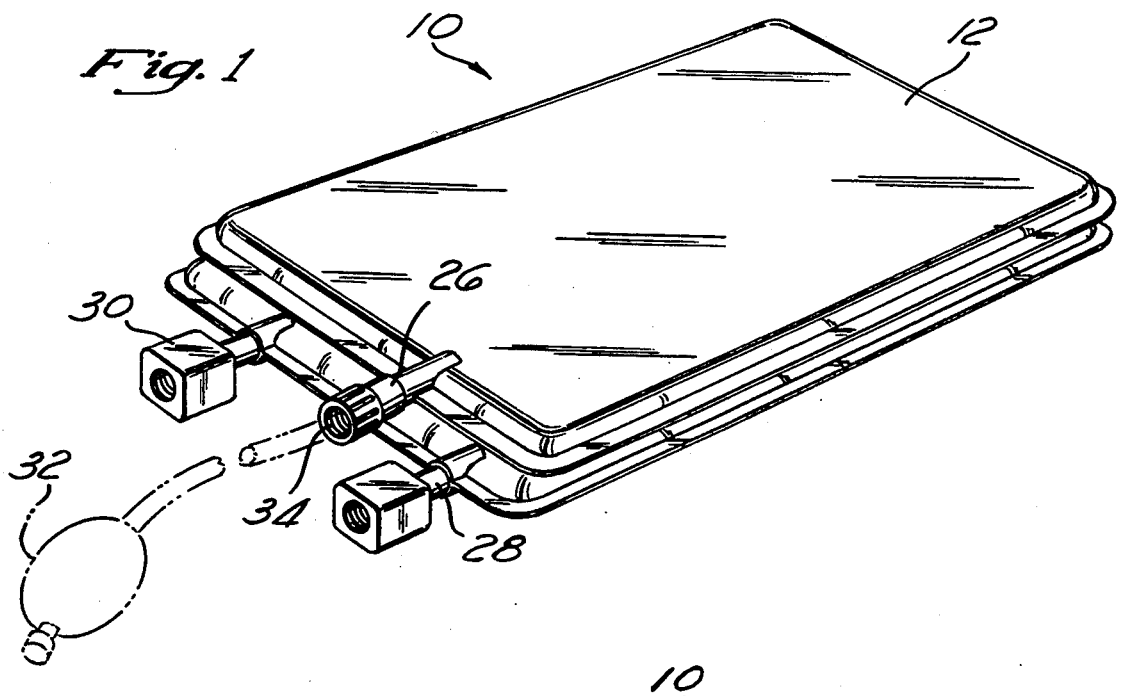
FIG. 1 is a perspective view of the flexible bladder member of the fluid therapy device.
Figure 2:
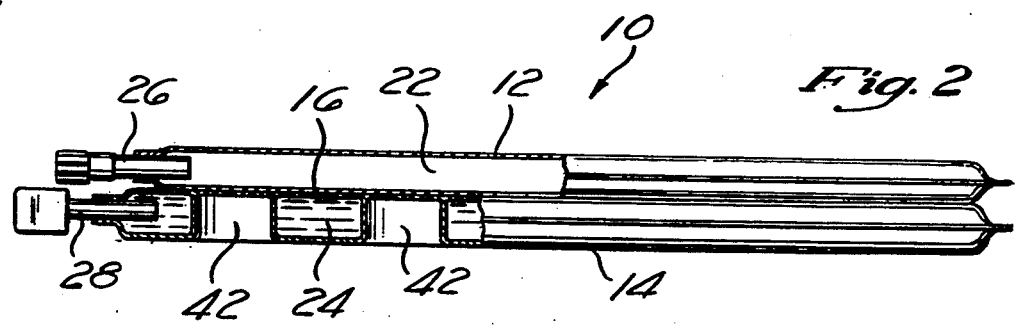
FIG. 2 is a partial cross-sectional view of the bladder member shown FIG. 1.

Referring now to the drawings wherein the showings are for purposes of illustrating preferred embodiments of the present invention only, and not for purposes of limiting the same, FIGS. 1 and 2 illustrate a flexible bladder member 10 of the fluid therapy device constructed in accordance with the present invention. In the preferred embodiment, the flexible bladder member 10 comprises an outer wall 12 and an inner wall 14. Positioned between the outer and inner walls 12, 14 is an intermediate wall 16. Defined between the outer wall 12 and intermediate wall 16 is an outer chamber 22, while defined between the inner wall 14 and intermediate wall 16 is an inner chamber 24. The outer and inner chambers 22, 24 defined within the bladder member 10 are independently inflatable. In this respect, fluidly coupled to the outer chamber 22 is an inlet/outlet valve port 26. Additionally, fluidly coupled to the inner chamber 24 is an inlet valve port 28 and an outlet valve port 30.

In the preferred embodiment, the outer chamber 22 of the bladder member 10 is adapted to be selectively inflated with air. The inflation of the outer chamber 22 with air is preferably accomplished via the utilization of a hand-held air pump 32 which may be fluidly coupled to the inlet/outlet valve port 26, as seen in FIG. 1. Advantageously, the inlet/outlet valve port 26 includes a purge mechanism 34 associated therewith to prevent the over-inflation of the outer chamber 22 with air.

The inner chamber 24 of the bladder member 10 is preferably filled with cold water. The infusion of water into the inner chamber 24 is preferably accomplished via the coupling of a portable water pumping apparatus 36 to the inlet valve port 28 thereof. Importantly, the water pumping apparatus 36 may be simultaneously coupled to the inlet and outlet valve ports 28, 30 of the inner chamber 24 to circulate cold water therethrough. The structure of the water pumping apparatus 36 and the manner in which water is circulated through the inner chamber 24 thereby will be discussed in greater detail below.

In the preferred embodiment, the inner wall 14 includes a multiplicity of recessed portions 42 formed therein for channeling water through the inner chamber 24 and preventing the inner wall 14 from bulging excessively when the inner chamber 24 is filled with water. As seen in FIG. 2, each of the recessed portions 42 formed within the inner wall 14 of the bladder member 10 includes a bottom wall portion which is affixed to the intermediate wall, thus defining a multiplicity of column-like supports within the inner chamber 24. In the preferred embodiment, the bottom walls of the recessed portions 42 are affixed to the intermediate wall 16 via a heat-bonding process, though it will be recognized that other affixation methods such as the use of adhesives may also be utilized. Advantageously, due to the affixation of the bottom walls of the recessed portions 42 to the intermediate wall 16, the inner wall 14 is prevented from bulging outwardly away from the intermediate wall 16 when the inner chamber 24 is filled with hot or cold water. In the bladder member 10, no recessed portions are provided in the outer wall 12 due to the desirability of having the outer chamber 22 "balloon" when filled with air via the pump 32. In this respect, the ballooning of the outer chamber 22 causes the inner chamber 24, and more particularly the inner wall 14, to be tightly compressed against and conform to a particular area of the user's body, as will hereinafter be described.

In addition to preventing the inner wall 14 from bulging outwardly away from the intermediate wall 16, the support columns defined within the inner chamber 24 by the affixation of the bottom walls of the recessed portions 42 to the intermediate wall 16 further define flow paths for water infused into the inner chamber 24 which facilitates the complete and uniform expansion thereof when filled. In this respect, the inner chamber support columns create flow paths which channel the water throughout the entire inner chamber 24 when the same is infused thereinto via the inlet valve port 28, and prevent the water from flowing directly from the inlet valve port 28 to the outlet valve port 30.

The bladder member 10 is preferably fabricated from a flexible material such as rubber, vinyl, urethane, or polyvinyl chloride, although it will be recognized that other materials possessing resilient properties may also be utilized. Additionally, the bladder member 10 may be fabricated from two independent bladder sections, one of which comprises an air bladder having an inlet/outlet valve port coupled thereto, and the other being a water bladder having independent inlet and outlet valve ports fluidly coupled thereto and recessed portions formed within one of the planar walls thereof. In this respect, the separate air and water bladders may be rigidly affixed to each other via adhesives or heat bonding so as to form a resultant bladder member having the same structure as the bladder member 10 shown in FIGS. 1 and 2.

In the preferred embodiment, the bladder member 10 is used in combination with a flexible or rigid orthopedic brace or sleeve for maintaining the bladder member 10 in a desired orientation relative to and in generally abutting contact with a selected region of the body. Though the bladder member 10 as depicted in FIG. 1 has a generally rectangular configuration, the same may be fabricated in shapes to fit into or on any flexible or rigid orthopedic brace, plus all fiberglass and plaster casts. As will be recognized, those bladder members used in association with plaster and fiberglass casts would be of a disposable nature, since once the cast is cut off of the body, the bladder member associated therewith would be rendered unusable.

Referring now to FIGS. 6–16, the bladder member 10 is depicted in various shapes which are adapted to accommodate different regions of the human body. As previously indicated, when the bladder member 10 is formed in the manner shown in FIGS. 6–16, the same will typically be utilized in conjunction with a flexible brace or support for maintaining the bladder member 10 in abutting contact with the region of the body which it is formed to accommodate. Generally, the backing material of the flexible brace or support with which the bladder member 10 is utilized must have some structural strength to limit the amount of "ballooning" of the outer chamber 22 which occurs when the same is inflated. One such material that provides the required support is sold under the trademark CORDURA. Since the hot or cold water for facilitating the desired therapeutic treatment of the body area is infused into the inner chamber 24, the bladder member 10 is interfaced to the cast or flexible brace/support such that the inner wall 14 thereof is directly abutted against, i.e. faces, the skin. Since the inner wall 14 is in direct contact with the skin, the same is preferably lined with a material such as "COOL MAX" to wick away any moisture that could cause infection or dampness, particularly when the bladder member 10 is interfaced to a cast.

Figure 6:
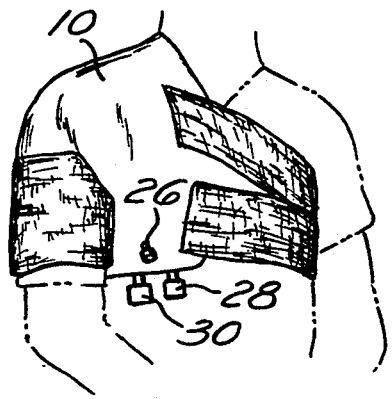
FIG. 6 is a perspective view of a shoulder embodiment of the bladder member.
Figures 7, 8:
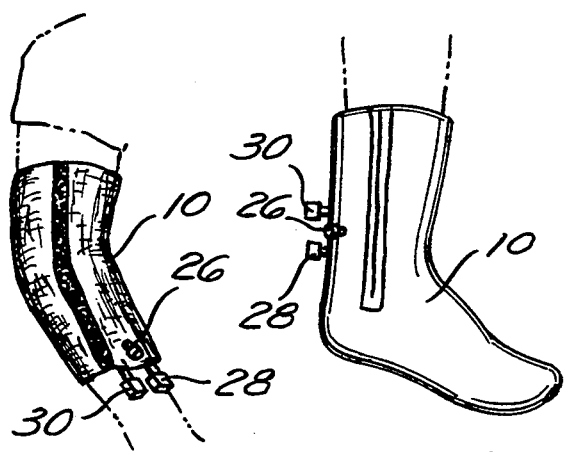
FIG. 7 is a perspective view of an elbow embodiment of the bladder member.
FIG. 8 is a perspective view of an ankle embodiment of the bladder member.
Figure 9:
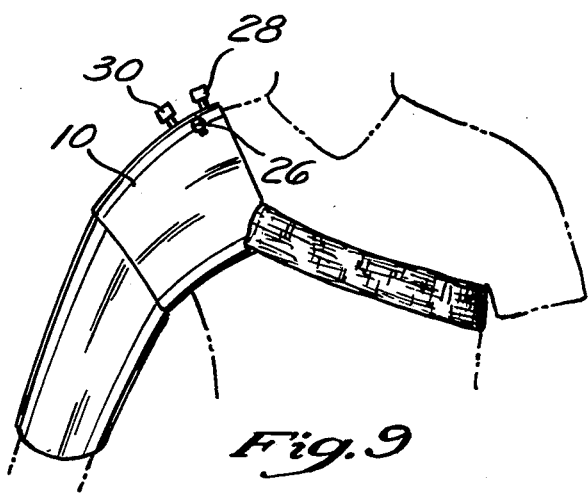
FIG. 9 is a perspective view of a shoulder/arm embodiment of the bladder member.
Figure 11:
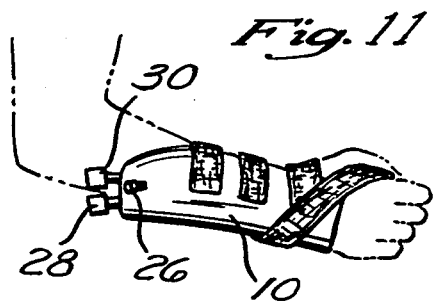
FIG. 11 is a perspective view of a wrist embodiment of the bladder member.
Figure 12:
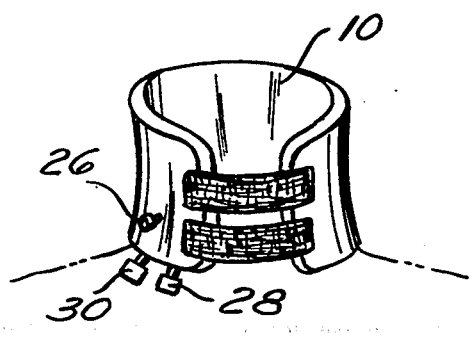
FIG. 12 is a perspective view of a neck embodiment of the bladder member.
Figure 13:
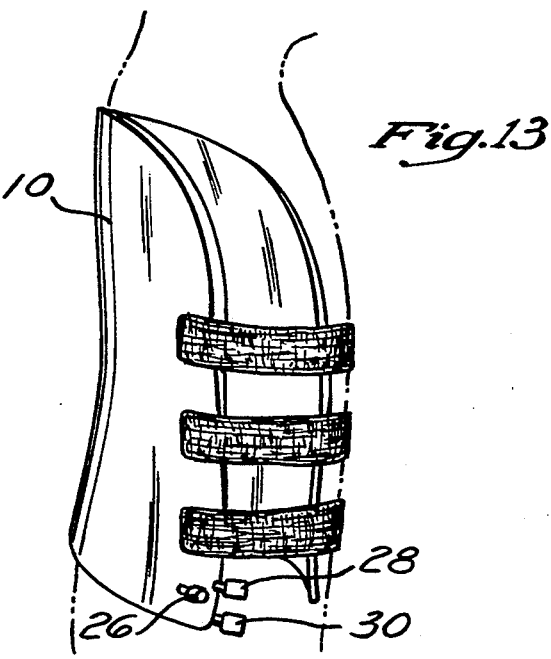
FIG. 13 is a perspective view of a full spinal embodiment of the bladder member.
Figure 14:
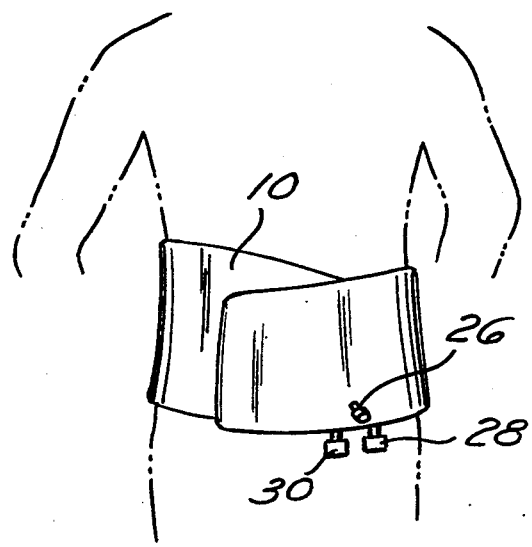
FIG. 14 is a perspective view of a lumbar embodiment of the bladder member.
Figure 15:
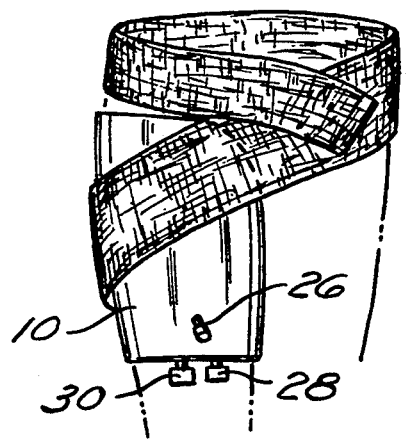
FIG. 15 is a perspective view of a groin/hip flexor embodiment of the bladder member.
Figure 16:
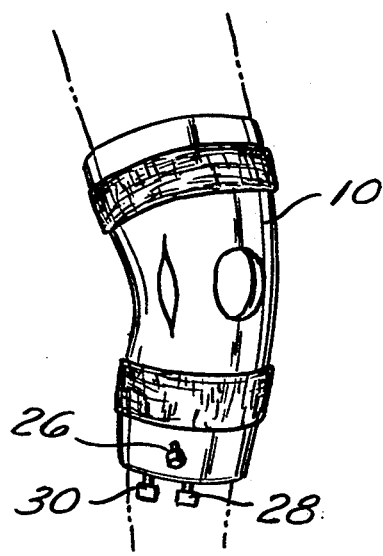
FIG. 16 is a perspective view of a knee embodiment of the bladder member.

In particular, FIG. 6 depicts the formation of the bladder member 10 to accommodate the shoulder, while in FIG. 7, the bladder member 10 is formed to accommodate the elbow. In FIG. 8, the bladder member 10 is formed generally in the shape of a sock to accommodate the ankle, while in FIG. 9, the bladder member is formed to accommodate the shoulder/arm. FIG. 11 depicts the formation of the bladder member 10 to suit the wrist, while FIG. 12 depicts the bladder member 10 as formed to extend about the neck. FIG. 13 depicts a full spinal embodiment of the bladder member 10, while FIG. 14 depicts a lumbar embodiment of the bladder member 10 which is extensible about the waist and lower back of the wearer. FIG. 15 depicts a groin-/hip flexor embodiment of the bladder 10, while in FIG. 16 the bladder member 10 is formed for use in a conventionally configured knee brace to accommodate the knee. Finally, in FIG. 10, the bladder member is formed to accommodate the wearer's calf. In each of the embodiments of the bladder member 10 depicted in FIG. 6–16, the same is incorporated into a flexible brace or sleeve. As such, the recessed portions 42 formed within the inner wall 14 are not visually apparent.

Figure 3:
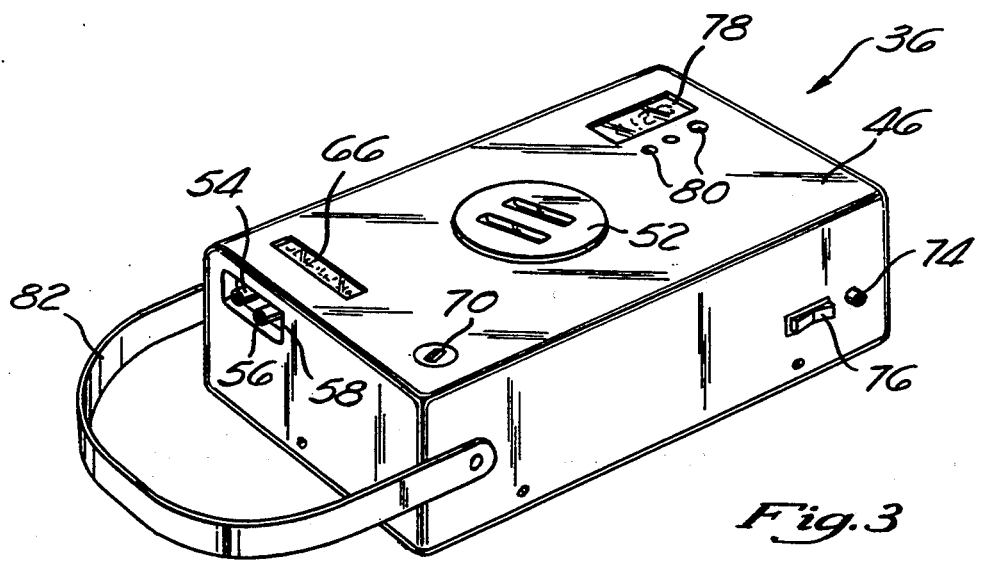
FIG. 3 is a perspective view of a water pumping apparatus used in conjunction with the bladder member shown in FIGS. 1 and 2.
Figure 4:
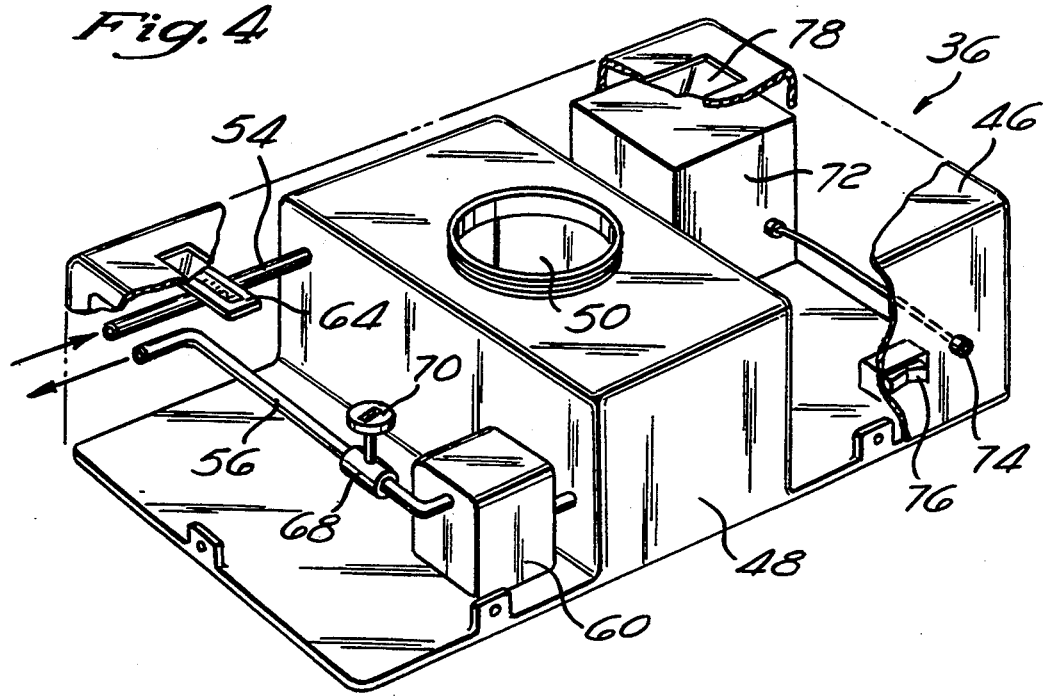
FIG. 4 is a perspective cut-away view illustrating the components disposed within the housing of the water pumping apparatus shown in FIG. 3.

Referring now to FIGS. 3 and 4, the water pumping apparatus 36 used in conjunction with the bladder member 10 in the present fluid therapy system preferably comprises a housing 46 having a generally rectangular configuration. Disposed within the housing 46 and centrally positioned therewithin is a generally rectangular water-retaining reservoir 48 which defines an inlet opening 50 normally enclosed by a circular reservoir cover 52 threadably engaged thereto. The pumping apparatus 36 further comprises an inlet line 54 having a first end protruding slightly outwardly from the housing 46 and a second end fluidly coupled to the reservoir 48. Also included is an outlet line 56 having a first end fluidly coupled to the reservoir 48 and a second end protruding slightly outwardly from the housing 46. As best seen in FIG. 3, the first end of the inlet line 54 and the second end of the outlet line 56 reside within a recess 58 defined within a laterally extending side wall of the housing 46.

Disposed within the housing 46 is a pump 60 which is fluidly coupled within the outlet line 56 intermediate the first and second ends thereof. The pump 60, when activated, is adapted to pump water from within the reservoir 48 to the second, external end of the outlet line 56. Fluidly coupled to the inlet line 54 intermediate the first and the second ends thereof is a temperature gauge 64 including a display portion 66 which is viewable from the exterior of the housing 46 through an elongate slot disposed in a corner region of the top surface thereof, underneath which the display portion 66 is positioned. The temperature gauge 64 is adapted to display temperature readings on the display portion 66 corresponding to the temperature of the water flowing from the inner chamber 24 to the reservoir 48 via the inlet line 54. Also fluidly coupled to the outlet line 56 intermediate the second end thereof and the pump 60 is an adjustable flow control valve 68 which includes a rotatable head portion 70 residing within a complimentary aperture disposed within the top surface of the housing 46. The flow control valve 68 is adapted to regulate the flow of water through the outlet line 56. In this respect, rotation of the head portion 70 in a first direction reduces the flow of water through the outlet line 56, while rotation of the head portion 70 in a second direction opposite the first direction increases the flow of water through the outlet line 56.

In addition to the foregoing components, the water pumping apparatus 36 includes a programmable control unit 72 which is disposed within the housing 46 and electrically interfaced to the pump 60, and temperature gauge 64. The control unit 72 itself comprises a timer/computer which is supplied with power via an AC/DC adapter 74 disposed on a longitudinal side wall of the housing 46, and is selectively activated via an On/Off switch 76 disposed adjacent the adapter 74. The control unit 72 further includes a display clock 78 associated therewith which is viewable through an elongate slot disposed in the top surface of the housing 46. The control unit 72 is programmable via a plurality of function buttons 80 disposed within the top surface of the housing 46 adjacent the display clock 78. To aid in the transport of the water pumping apparatus 36, attached to the opposed longitudinal side walls of the housing 46 is an arcuate handle member 82.

Figure 5:
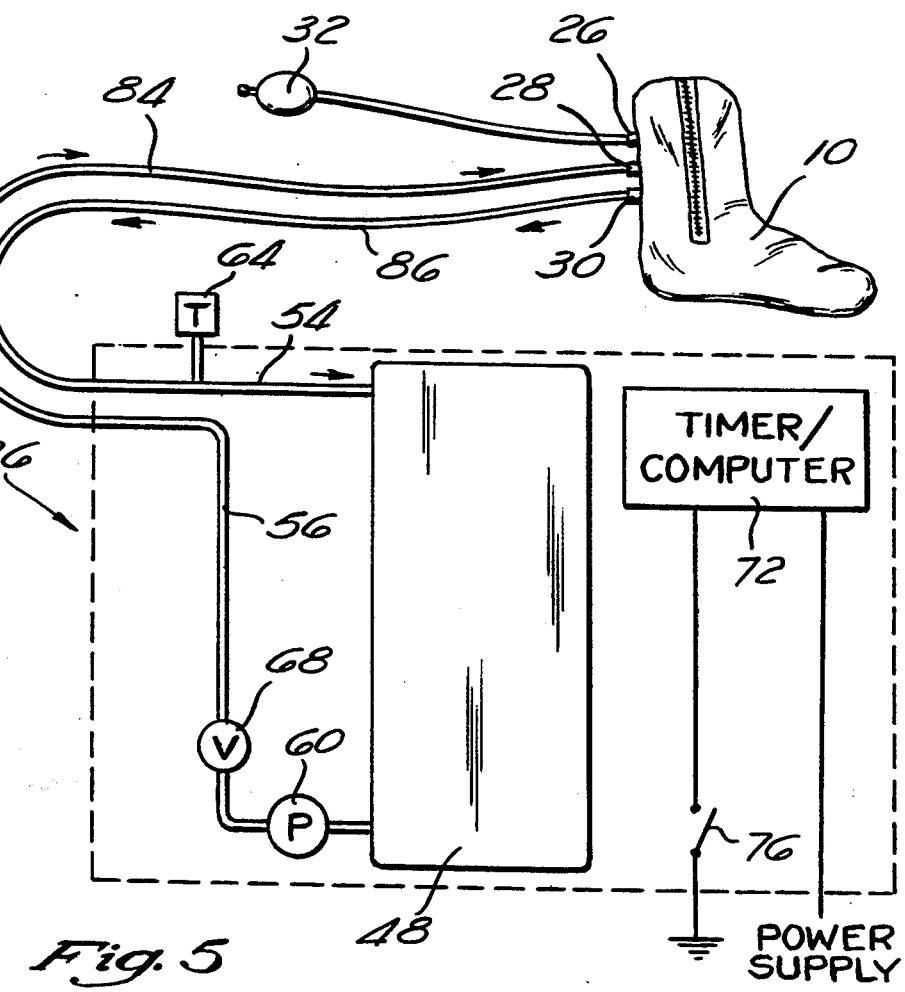
FIG. 5 is a schematic illustrating the operation of the fluid therapy device.

Referring now to FIG. 5, the fluid therapy device is preferably utilized by first applying the bladder member 10 to the particular region of the body which it is configured to accommodate. After the bladder member 10 has been secured to the body such that the inner wall 14 thereof is in direct contact with the skin, the air pump 32 is coupled to the inlet/outlet valve port 26 and used to inflate the outer chamber 22 with air. The inlet valve port 28 is then coupled to the second end of the outlet line 56 via a first flow line 84, with the outlet valve port 30 being coupled to the first end of the inlet line 54 via a second flow line 86.

To facilitate the circulation of cold water through the inner chamber 24 of the bladder member 10, the switch 76 is actuated to the "ON" position thus supplying power to the control unit 72, which in turn activates the pump 60 thus causing the cold water to be pumped from the reservoir 48 into the inner chamber 24 via the first flow line 84, and from the inner chamber 24 back into the reservoir 48 via the second flow line 86. The duration of the cold therapy is programmed into the control unit 72 via the function buttons 80 by a physician, based on the patient's therapeutic needs. The temperature of the water circulated through the inner chamber 24 is displayed on the display portion 66 of the temperature gauge 64, with the time span of the therapy being displayed on the display clock 78. To initiate the application of cold therapy, the reservoir 48 is filled with tap water, with ice or a "blue block" being placed into the water within the reservoir 48. Subsequent to the addition of the ice or "blue block" into the water, the water pumping apparatus 36 is activated via the switch 76. The control unit 72 then circulates the cold water through the inner chamber 24 for the length of time programmed thereinto. During the circulation of cold water through the inner chamber 24, the control unit 72 may be programmed to cycle the pump 60 on and off thus creating a pulsation effect. In the preferred embodiment, the reservoir 48 is insulated to aid in maintaining the temperature of the water therewithin. Advantageously, the water pumping apparatus 36 is configured such that the cold water will not come in contact with the control unit 72.

Referring now to FIG. 20, there is schematically depicted a water pumping apparatus 100 constructed in accordance with a second embodiment of the present invention which may be utilized as an alternative to the previously described water pumping apparatus 36, and is adapted to selectively circulate hot or cold water through the inner chamber 24 of the bladder member 10. In the second embodiment, the water pumping apparatus 100 also comprises a rectangularly configured housing sized similarly to the housing 46 of the water pumping apparatus 36. Disposed within the housing of the water pumping apparatus 100 is a generally rectangular water-retaining reservoir 102 which defines a separate hot water basin 104 and cold water basin 106. Though not shown, the hot and cold water basins 104, 106 each define inlet openings which are normally enclosed by a pair of circularly configured reservoir covers threadably engaged thereto.

The pumping apparatus 100 further comprises a first inlet line 108 having a first end protruding slightly outwardly from the housing thereof and a second end fluidly coupled to the hot water basin 104. Also included is a first outlet line 110 having a first end fluidly coupled to the hot water basin 104 and a second end protruding slightly outwardly from the housing. Disposed within the housing and fluidly coupled within the first outlet line 110 intermediate the first and second ends thereof is a first pump 112. The first pump 112, when activated, is adapted to pump water from within the hot water basin 104 to the second, external end of the first outlet line 110. Fluidly coupled to the first inlet line 108 intermediate the first and second ends thereof is a first temperature gauge 114 which includes a display portion viewable from the exterior of the housing through an elongate slot disposed within a corner region of the top surface thereof, underneath which the display portion is positioned. The first temperature gauge 114 is adapted to display temperature readings which correspond to the temperature of the hot water flowing into the hot water basin 104 via the first inlet line 108. Also fluidly coupled to the first outlet line 110 intermediate the second end thereof and the first pump 112 is a first adjustable flow control valve 116 which, like the previously described flow control valve 68, includes a rotatable head portion residing within a complementary aperture disposed within the top surface of the housing 30 of the pumping apparatus 100. The first flow control valve 116 is adapted to regulate the flow of water through the first outlet line 110. In this respect, rotation of the head portion of the first flow control valve 116 in a first direction reduces the flow of water through the first outlet line 110, while rotation of the head portion in a second direction opposite the first direction increases the flow of water through the first outlet line 110. Disposed within the hot water basin 104 is a heater 118 which, when activated, heats the water stored within or being circulated through the hot water basin 104.

In addition to the first inlet and outlet lines 108, 110, the pumping apparatus 100 comprises a second inlet line 120 having a first end protruding slightly outwardly from the housing of the pumping apparatus 100 and a second end fluidly coupled to the cold water basin 106. Also included is a second outlet line 122 having a first end fluidly coupled to the cold water basin 106 and a second end protruding slightly outwardly from the housing. Though not shown, the first ends of the first and second inlet lines 108, 120 and the second ends of the first and second outlet lines 110, 122 preferably reside within a recess defined within a laterally extending side wall of the housing of the pumping apparatus 100. Fluidly coupled within the second outlet line 122 intermediate the first and second ends thereof is a second pump 124 which, when activated, is adapted to pump water from within the cold water basin 106 to the second, external end of the second outlet line 122. Fluidly coupled to the second inlet line 120 intermediate the first and second ends thereof is a second temperature gauge 126 which also includes a display portion viewable from the exterior of the housing via an elongate slot disposed in a corner region of the top surface thereof, underneath which the display portion is positioned. The second temperature gauge 126 is adapted to display temperature readings which correspond to the temperature of the cold water flowing into the cold water basin 106 via the second inlet line 120. Also fluidly coupled to the second outlet line 122 intermediate the second end thereof and the second pump 124 is a second adjustable flow control valve 128 which includes a rotatable head portion residing within a complementary aperture disposed within the top surface of the housing. Similar to the first flow control valve 116, the second flow control valve 128 is adapted to regulate the flow of cold water through the second outlet line 122. In this respect, rotation of the head portion of the second flow control valve 128 in a first direction reduces the flow of water through the second outlet line 122, while rotation of the head portion in a second direction opposite the first direction increases the flow of water through the second outlet line 122.

Figure 17:
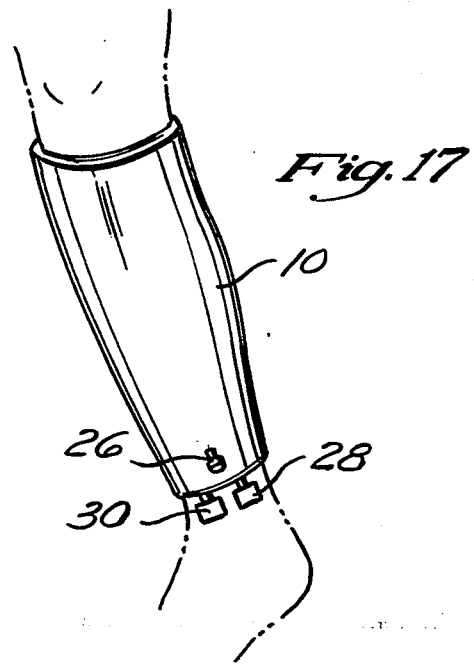
FIG. 17 is a perspective view of a flexible bladder member constructed in accordance with a second embodiment of the present invention.

In addition to the foregoing components, the water pumping apparatus 100 includes a programmable control unit 130 which is disposed within the housing thereof and electrically interfaced to the first and second pumps 112, 124, heater 118, and first and second temperature gauges 114, 126. The control unit 130 itself comprises a timer/computer which is supplied with power via an AC/DC adapter disposed on a side wall of the housing, and is selectively activated via a corresponding ON/OFF switch. Like the previously described control unit 72, the control unit 130 includes a display clock associated therewith which is viewable through an elongate slot disposed in the top surface of the housing, as well as a plurality of function buttons to facilitate the programming of the control unit 130. Finally, an arcuate handle member is preferably attached to the opposed longitudinal side walls of the housing of the pumping apparatus 100 to aid in the transport thereof, Though the water pumping apparatus 100 may be utilized in conjunction with the previously described bladder member 10, the same is preferably utilized in conjunction with a bladder member 200 which is constructed in accordance with a second embodiment of the present invention and is adapted to have both hot and cold water selectively circulated therethrough. As seen in FIGS. 17, 18, and 19, the bladder member 200 preferably comprises an outer wall 202 and an inner wall 204. Positioned between the outer and inner walls 202, 204 is an intermediate wall 206. Defined between the outer wall 202 and the intermediate wall 206 is an outer chamber 208, while defined between the inner wall 204 and the intermediate wall 206 is an inner chamber 210. Positioned within the inner chamber 210 between the inner wall 204 and intermediate wall 206 is a flexible membrane or baffle 212 which divides the inner chamber 210 into a hot water receiving region 214 and a cold water receiving region 216, each of which are independently inflatable. In this respect, the hot water region 214 is defined between the baffle 212 and the intermediate wall 206, while the cold water region 216 of the inner chamber 210 is defined between the baffle 212 and the inner wall 204. Fluidly coupled to the outer chamber 208 is an inlet/outlet valve port 218. Additionally, fluidly coupled to the hot water region 214 is a first inlet valve port 220 and a first outlet valve port 222, while fluidly coupled to the cold water region 216 is a second inlet valve port 224 and a second outlet valve port 226.

In the bladder member 200, the outer chamber 208 is adapted to be selectively inflated with air. The inflation of the outer chamber 208 with air is preferably accomplished via the utilization of the previously described hand-held air pump 32 which may be fluidly coupled to the inlet/outlet valve port 218. Like the inlet/outlet valve port 26 previously described, the inlet/outlet valve port 218 preferably includes a purge mechanism 228 associated therewith to prevent the over-inflation of the outer chamber 208 with air.

The infusion of hot water into the hot water region 214 of the inner chamber 210 and the infusion of cold water into the cold water region 216 of the inner chamber 210 is preferably accomplished via the coupling of the water pumping apparatus 100 to the bladder member 200. The water pumping apparatus 100 is preferably simultaneously coupled to the first inlet and outlet valve ports 220, 222 of the hot water region 214 and second inlet and outlet valve ports 224, 226 of the cold water region 216 to selectively circulate hot or cold water therethrough.

Like the bladder member 10 previously described, the bladder member 200 is preferably fabricated from a flexible material, such as rubber, vinyl, urethane, or polyvinyl chloride, although other materials possessing resilient properties may also be utilized. Additionally, the bladder member 200 may be fabricated from two independent bladder sections, one of which comprises an air bladder having an inlet/outlet valve port coupled thereto, and the other being a water bladder defining separate hot and cold water regions and independent inlet and outlet valve ports fluidly coupled to each of the regions. The separate air and water bladders may be rigidly affixed to each other via adhesives or heat bondings so as to form a resultant bladder member having the same structure as the bladder member shown in FIGS. 17, 18, and 19. Additionally, like the previously described bladder member 10, the bladder member 200 is preferably used in combination with a flexible or rigid orthopedic brace or sleeve for maintaining the bladder member 200 in a desired orientation relative to and in generally abutting contact with a selected region of the body. Though the bladder member 200, as depicted in FIG. 17, has a generally rectangular configuration, the same may be fabricated in shapes to fit into or on any flexible or rigid orthopedic brace, plus all fiberglass and plaster casts. In particular, the bladder member 200 may be formed to accommodate any of the body regions as shown in FIGS. 6-16.

Referring again to FIG. 20, the bladder member 200 is utilized by initially applying the same to the particular region of the body which it is configured to accommodate. After the bladder member 200 has been secured to the body such that the inner wall 204 thereof is in direct contact with the skin, the air pump 32 is coupled to the inlet/outlet valve port 218 and used to inflate the outer chamber 208 with air. The first inlet valve port 220 is then coupled to the second end of the first outlet line 110 via a first flow line 230, with the first outlet valve port 222 being coupled to the first end of the first inlet line 108 via a second flow line 232. Similarly, the second inlet valve port 224 is coupled to the second end of the second outlet line 122 via a third flow line 234, while the second outlet valve port 226 is fluidly coupled to the first end of the second inlet line 120 via a fourth flow line 236.

To facilitate the circulation of hot or cold water through the inner chamber 210 of the bladder member 200, the switch of the pumping apparatus 100 is actuated to the "ON" position, thus supplying power to the control unit 130, which in turn activates either the first or second pumps 112, 124. In this respect, the activation of the first pump 112 by the control unit 130 causes hot water to be pumped from the hot water basin 104 into the hot water region 214 of the inner chamber 210 via the first outlet line 110, and from the hot water region 214 back into the hot water basin 104 via the first inlet line 108. Similarly, the activation of the second pump 124 by the control unit 130 causes cold water to be pumped from the cold water basin 106 into the cold water region 216 of the inner chamber 210 via the second outlet line 122, and from the cold water region 216 back into the cold water basin 106 via the second inlet line 120. The duration of the heat therapy or the cold therapy is programmed into the control unit 130 via the function buttons associated therewith by a physician, based on the patient's therapeutic needs. The temperature of the water circulated through the hot water region 214 is displayed on the display portion of the first temperature gauge 114, while the temperature of the water circulated through the cold water region 216 is displayed on the display portion of the second temperature gauge 126. Additionally, the time span of either the heat or cold therapy, i.e., the activation time of either the first or second pumps 112, 124, is displayed on the display clock of the pumping apparatus 100.

As previously explained, the pumping apparatus 100 may be utilized to selectively circulate hot or cold water through the bladder member 200. Advantageously, the control unit 130 may be provided with preset rehabilitative programs which can be selectively modified or changed by the attending physician. In particular, by modifying the program of or changing a memory chip associated with the control unit 130, the pumping apparatus 100 may be caused to circulate hot and cold water, separately or in sequence, through the bladder member 200. As will be recognized, in those treatment modalities wherein hot and cold water is circulated through the bladder member 200 in sequence, it would be desirable to completely drain the hot water from the hot water region 214 prior to the circulation of cold water through the cold water region 216. Similarly, it would be desirable to completely drain the cold water from the cold water region 216 prior to circulating hot water through the hot water region 214. Such selective drainage of the hot and cold water regions 214, 216 is facilitated by the baffle 212 disposed within the inner chamber 210.

As seen in FIG. 18, the circulation of cold water through the cold water region 216 causes the baffle 212 to be expanded inwardly into contact with the intermediate wall 206, thus causing any residual hot water remaining in the hot water region 214 to be forced therefrom and back into the hot water basin 104 via the first outlet line 110. As seen in FIG. 19, the circulation of hot water through the hot water region 214 of the inner chamber 210 forces the baffle 212 outwardly into contact with the inner wall 204, thus forcing any residual cold water within the cold water region 216 therefrom and back into the cold water basin 106 via the second outlet line 122. As such, due to the inclusion of the baffle 212, when hot water is circulated through the hot water region 214, the cold water is substantially drained from the cold water region 216. Similarly, when cold water is circulated through the cold water region 216, the hot water is substantially drained from the hot water region 214.

In those applications where heat therapy is desired, the hot water basin 104 is filled with tap water by removing the cover from the inlet opening thereof. As the water is circulated through the hot water basin 104, the same is heated via the heater 118 disposed therein to a temperature programmed into the control unit 130 (to a maximum of 107° F.). To facilitate the application of cold therapy, the cold water basin 106 is filled with tap water, with ice or a "blue block" being placed into the water within the cold water basin 106. As will be recognized, for the application of cold therapy, the control unit 130 is programmed not to activate the first pump 112 or heater 118, but rather only the second pump 124. Additionally, for the application of heat therapy, the control unit 130 is programmed not to activate the second pump 124, but rather only the heater 118 and first pump 112. For application of both heat and cold therapy in sequence, the control unit 130 is programmed to selectively activate the first and second pumps 112, 124 and heater 118, depending upon the programmed time duration of each of the therapies. During the circulation of hot and/or cold water through the bladder member 200, the control unit 130 may be programmed to cycle the first pump 112 and/or second pump 124 on and off thus creating a pulsation effect. The reservoir 102 is insulated to aid in maintaining the temperature of the water therewithin. Advantageously, the water pumping apparatus 100 is configured such that hot or cold water will not come into contact with the control unit 130.

Referring now to FIG. 21, partially illustrated is a bladder member 300 constructed in accordance with a third embodiment of the present invention. The bladder member 300 is substantially similar to the bladder member 200 previously described, and defines an outer chamber 302 adapted to be selectively inflated with air, and an inner chamber 304 which defines hot and cold water regions therewithin. However, in the third embodiment, the bladder member 300 is preferably fabricated from two independent bladder sections, one of which comprises an air bladder 306 defining the outer chamber 302, and the other being a water bladder 308 which defines the inner chamber 304, and hence, the hot and cold water regions therewithin.

In the bladder member 300, the separate air and water bladders 306, 308 are rigidly affixed to each other via adhesives or heat bonding so as to form a resultant bladder member having a structure similar to the previously described bladder member 200. However, prior to the attachment of the air and water bladders 306, 308 to each other, the water bladder 308 is encapsulated within a flexible envelope 310. As such, when the air bladder 306 is attached to the water bladder 308, a portion of the envelope 310 is captured between the air and water bladders 306, 308. Advantageously, the envelope 310 is utilized to capture moisture or condensation which forms upon the exposed surfaces of the water bladder 308, particularly when cold water is circulated therethrough. In this respect, the envelope 310 captures such moisture, thus preventing the same from coming into contact with the wearer's body and preventing the adverse side effects associated with the presence of moisture intermediate the skin and the inner surfaces of the brace or cast. In the bladder member 300, the envelope 300 may be periodically drained via an outlet port 312 fluidly coupled thereto.

The fluid therapy system of the present invention can be used postoperatively in orthopedic and other surgical applications. The heat or cold therapy modalities may be initiated postoperatively and continued without the need of removing the cast or brace from the patient into which the bladder member 10, 200 is placed. Advantageously, the inflation of the outer chamber 22, 208 with air provides controlled compression to help reduce swelling, and also prevents the bladder member 10, 200 from sagging as the swelling reduces and thus not conforming correctly to the body region to which it is applied, as would normally occur when only the inner chamber 24, 210 is filled with water, or water is circulated therethrough. As such, the inflated outer chamber 22, 208 maintains the water filled inner chamber 24, 210 in place on and in direct contact with the skin of the patient. The filling of the inner chamber 24, 210 with hot or cold water, or the circulation of hot or cold water therethrough, provides the cold or hot therapeutic modalities needed to reduce swelling and pain. As the swelling reduces, the outer chamber 22, 208 may be inflated with additional quantities of air to take up the extra space caused by the reduction in swelling. As will be recognized, the water pumping apparatus 36, 100 may be used to fill the inner chamber 24, 210 with hot or cold water, rather than being utilized to circulate the water therethrough. Additionally, circulation units of other manufacturers may also be utilized as an alternative to the water pumping apparatus 36, 100.

The present invention is capable of providing virtually every heat or cold modality commonly prescribed by physicians. Due to the programmability of the water pumping apparatus 36, 100, a physician will be able to apply heat or cold therapy to a particular body region for a desired time duration. The water pumping apparatus 36, 100 can be rented to hospitals for emergency and surgical applications, or purchased by medical personnel such as therapists and chiropractors. In non-medical applications, the water pumping apparatus 36, 100 can be used in conjunction with built-in water pads for the base and back of seats such as seats included in trucks, buses, autos, aircraft, wheelchairs and in work seats (such as those used by telephone and computer operators). The present fluid therapy device may also be used in relation to veterinary applications.

Additional modifications and improvements of the present invention may also be apparent to those skilled in the art. Thus, the particular combination of parts described and illustrated herein is intended to represent only one embodiment of the invention, and is not intended to serve as limitations of alternative devices within the spirit and scope of the invention.

What is claimed is:

1. A therapy device comprising of a flexible bladder member with a portable fluid therapy device, said flexible bladder for use in combination:
   defining independently inflatable inner and outer chambers, with said inner chamber defining independently inflatable hot and cold water receiving regions any and, said bladder member comprising:
   an outer wall;
   an inner wall;
   an intermediate wall positioned between said inner and outer walls; and
   a flexible baffle positioned between said intermediate and inner walls;
   said outer chamber being defined between said outer and intermediate walls, said hot water region being defined between said baffle and said intermediate wall, and said cold water region being defined between said baffle and said inner wall;
   a first inlet valve port fluidly coupled to the hot water region of said inner chamber;

a first outlet valve port fluidly coupled to the hot water region of said inner chamber;

a second inlet valve port fluidly coupled to the cold water region of said inner chamber;

a second outlet valve port fluidly coupled to the cold water region of said inner chamber; and an inlet/outlet valve port fluidly coupled to said outer chamber.

2. The device of claim 1 further in combination with a portable water pumping apparatus for selectively infusing water into the hot and cold water regions of said inner chamber via said first and second inlet valve ports.

3. The device of claim 2 wherein said water pumping apparatus is fluidly connectable to the first inlet and outlet valve ports of the hot water region of the inner chamber and adapted to circulate hot water therethrough, and is fluidly connectable to the second inlet and outlet valve ports of the cold water region of the inner chamber and adapted to circulate cold water therethrough.

4. The device of claim 3 wherein said portable water pumping apparatus comprises:

a housing;

a water-retaining reservoir disposed within said housing, said water-retaining reservoir defining a hot water basin and a cold water basin;

a first inlet line having a first end protruding from said housing and a second end fluidly coupled to said hot water basin;

a first outlet line having a first end fluidly coupled to said hot water basin and a second end protruding from said housing;

a second inlet line having a first end protruding from said housing and a second end fluidly coupled to said cold water basin;

a second outlet line having a first end fluidly coupled to said cold water basin and a second end protruding from said housing;

a first pump disposed within said housing and fluidly coupled with said first outlet line intermediate the first and second ends thereof, said first pump being adapted to pump water from said hot water reservoir to the second end of said first outlet line when activated; and a second pump disposed with said housing and fluidly coupled within said second outlet line intermediate the first and second ends thereof, said second pump being adapted to pump water from said cold water basin to the second end of said second outlet line when activated.

5. The device of claim 4 wherein said pumping apparatus further comprises:

a heater disposed within said hot water basin;

a first temperature gauge partially disposed within said housing and fluidly coupled to said first inlet line intermediate the first and second ends thereof, said first temperature gauge being adapted to display temperature readings corresponding to the temperature of the water pumped through said first inlet line; and a second temperature gauge partially disposed within said housing and fluidly coupled to said second inlet line intermediate the first and second ends thereof, said second temperature gauge being adapted to display temperature readings corresponding to the temperature of the water pumped through said second inlet line 6. The device of claim 5 wherein said pumping apparatus further comprises:

a first adjustable flow control valve partially disposed within said housing and fluidly coupled to said first outlet line intermediate the first pump and the second end of said first outlet line, said first flow control valve being adapted to regulate the flow of water through said first outlet line; and a second adjustable flow control valve partially disposed within said housing and fluidly coupled to said second outlet line intermediate the second pump and the second end of said second outlet line, said second flow control valve being adapted to regulate the flow of water through said second outlet line.

7. The device of claim 5 wherein said water pumping apparatus further comprises a programmable control unit disposed within said housing and electrically interfaced to said first and second pumps, said heater, and said first and second temperature gauges.

8. The device of claim 1 wherein said bladder member is fabricated from a flexible material selected from the group consisting of:

rubber;

vinyl;

urethane; and polyvinyl chloride.

9. The device of claim 2 further comprising a flexible envelope disposed about and encapsulating the inner wall, said envelope being adapted to capture condensation forming on said inner wall when water is circulated through the hot and cold water regions of said inner chamber.

10. The device of claim 9 further comprising an outlet valve fluidly coupled to said flexible envelope for selectively draining water therefrom.

* * * * *